United States Patent [19] [11] 4,208,354
Demosthene et al. [45] Jun. 17, 1980

[54] BORANE COMPLEXES

[75] Inventors: Claude G. Demosthene, Aramon; Christian R. Aspisi, Villeneuve-les-Avignon, both of France

[73] Assignee: Expansia, Paris, France

[21] Appl. No.: 945,511

[22] Filed: Sep. 25, 1978

[30] Foreign Application Priority Data

Oct. 1, 1977 [GB] United Kingdom ............... 40862/77
May 31, 1978 [GB] United Kingdom ............... 25653/78

[51] Int. Cl.$^2$ ................................................ C07F 5/02
[52] U.S. Cl. ........................................ 568/3; 568/825; 568/880; 568/899
[58] Field of Search ................................ 260/606.5 B

[56] References Cited

U.S. PATENT DOCUMENTS 3,928,293  12/1975  Crosby ........................... 260/606.5 B Primary Examiner—Helen M. S. Sneed
Attorney, Agent, or Firm—Eyre, Mann, Lucas & Just

[57] ABSTRACT

New bis-thioaralkyl/alkyl alkyl boranes for use in hydroboration and reduction reactions are disclosed. They have the formula:

$R_4R_3HB:R_1SASR_2:BHR_3R_4$ wherein:
A stands for a straignt, branched or cyclic hydrocarbon chain containing from 1 to 9 carbon atoms,
$R_1$ and $R_2$ stand each for a straight or branched alkyl rest containing up to 5 carbon atoms in the longest chain, or benzyl radicals optionally substituted by one or more lower alkyl containing up to 5 carbon atoms or a halogen, and
$R_3$ and $R_4$ stand for a hydrogen atom, a lower alkyl up to $C_6$ or a mono or bicycloalkyl group.

1 Claim, No Drawings

BORANE COMPLEXES

This invention relates to borane complexes for use in hydroboration and reduction reactions.

Hydroboration and reduction reactions are well-known to lead easily to various organic functions with generally quantitative yields and a very good selectivity of position for the fixation on the multiple bonds involved.

Most known hydroboration and reducing agents have the drawback of poor stability which hinders their marketing. The borane complexes of the invention are stable under normal temperature conditions, at least for many months.

This invention provides boranes of the general formula: $R_4R_3HB : R_1SASR_2 : BHR_3R_4$ wherein:

A represents a straight chain, branched chain or cyclic hydrocarbon residue containing from 1 to 9 carbon atoms, $R_1$ and $R_2$ each represents a straight chain or branched chain alkyl residue containing up to 5 carbon atoms in the longest chain, or a benzyl radical optionally substituted by one or more alkyl residue(s) containing up to 5 carbon atoms or by one or more halogen atoms, and $R_3$ and $R_4$ each represents a hydrogen atom, an alkyl residue containing up to 6 carbon atoms or a mono or bicycloalkyl group.

These compounds may be liquids or solids at room temperature. They are miscible with or soluble in various solvents such as benzene, diethyl ether, methylene dichloride, tetrahydrofuran and diglyme, and their concentrations in hydroboration factor is higher than those of the previously used hydroboration agents.

The complexes $H_3B : R_1SASR_2 : BH_3$ are at least as stable as boron methyl sulphide for instance.

The complexes $R_4R_3HB : R_1SASR_2 : BHR_3R_4$ need not necessarily be prepared in situ before setting the reaction as it was the case with the known parent compounds $(BHR_3R_4)$ such as thexylborane or disiamylborane for instance. They are therefore easier to handle.

The reactivity of the compounds in which the borane moiety is not substituted is comparable with that of boron methyl sulphide complex; the reactivity of the compounds in which the borane moiety is substituted is comparable with that of the correspondingly substituted known boranes; but in both cases, the reaction speeds are higher than with the previously known complexes.

Certain lower representatives of the family, i.e. those in which $R_1 = R_2 = CH_3$ with $A = CH_2$, $(CH_2)_2$ or $(CH_2)_3$ and $R_1 = R_2 = $ tertiobutyl with $A = CH_2$, have slightly different structure from the one above represented by retain all the mentioned advantages.

These compounds may be prepared by a method derived from that described by BROWN H. C. in "Organic Synthesis via Boranes" (Wiley Interscience, NEW YORK, N. Y. 1975), using similar apparatus.

More precisely, compounds according to this invention may be obtained by reacting, in an aprotic solvent, under an inert atmosphere, at a temperature lower than 40° C. and under stirring, a compound of the general formula $R_1SASR_2$, wherein $R_1$, $R_2$ and A are as hereinbefore defined with a borone of the general formula $(BHR_3R_4)_2$ wherein $R_3$ and $R_4$ are as hereinbefore defined. The compound $R_1SASR_2$ can be obtained from the corresponding commercial alkyl dithiols of general formula HSASH by S-alkylation with an aralkyl halide or an alkyl halide according to the method described by OVERBERGER and SCHILLER, J. Org. Chem 26, 4232 (1961) or by treatment of the commercial thiols with the appropriate dihalogenoalkane by classic methods or by phase transfer catalysis according to the method described by A. W. HERRIOT, Synthesis, P. 447, July 1975; the borane may be obtained by any of the well-known conventional routes or from a complex $BH_3$: LEWIS base; the substituted boranes may be obtained for instance by the method described by BROWN H. C. and MANDAL A. K., Synthesis, 2, 146, (1978) or that described by BROWN H. C., MANDAL A. K. and KULKARNI S. U., J. Org. Chem. 42, (8), 1932, (1977).

Additionally, those compounds in which $R_3$ and $R_4$ do not represent hydrogen can be prepared by reacting, under the conditions given above, a compound $H_3B:R_1SASR_2:BH_3$ with the appropriate alkenes. In this reaction the compound $H_3B:R_1SASR_2:BH_3$ is used as a hydroboration agent. This preparative process, and that described in the last preceding paragraph, are within the scope of the invention.

This invention also provides hydroboration processes and reduction processes and reduction processes wherein boranes of the general formula $R_4R_3HB:R_1SASR_2:BHR_3R_4$ as hereinbefore defined are used as the hydroboration agents or reducing agents respectively.

This invention is illustrated by the following examples:

EXAMPLE 1

1,2-bis thiomethyl ethane, diborane $R_1 = R_2 = CH_3$; $R_3 = R_4 = H$; $A = -(CH_2)_2-$ 55 g. (0.45 mol) of 1,2-bis thiomethyl ethane in 200 ml of methylene dichloride previously distilled on calcium hydride were poured into a 2-litre reactor maintained under nitrogen circulation. 0.5 mol of diborane $(B_2H_6)$ was slowly injected, over a period of one hour and under stirring, into the reactor.

The diborane was obtained from 28.5 g (0.75 mol) of sodium borohydride (purity: 98%) dissolved in 200 ml of diglyme previously distilled on lithium aluminium hydride, treated dropwise with 123 ml (1 mol) of boron trifluoride etherate also previously distilled. The mixture diglyme $BH_4Na-BF_3/(C_2H_5)_2O$ is heated at 60° C. for fifteen minutes.

The reaction mixture was then allowed to cool and nitrogen was injected into it for one hour. The mixture was concentrated under reduced pressure. The liquid thus obtained was stored at room temperature or, preferably, at a temperature slightly below room temperature in the presence of nitrogen. The identity and structure of this compound were confirmed by analysis as indicated after the examples. Yield 57 g (85%). This compound is a liquid.

EXAMPLE 2

1,4-bis thiomethyl butane, diborane $R_1 = R_2 = CH_3$; $R_3 = R_4 = H$; $A = -(CH_2)_4-$ The title compound was obtained in 82% yield by operating as in Example 1 but using 1,4-bis thiomethyl butane instead of 1,2-bis thiomethyl ethane. The identity and structure of this compound were confirmed by analysis as indicated after the examples. This compound is a liquid.

EXAMPLE 3

1,9-bis thiomethyl nonane, diborane $R_1=R_2=CH_3$; $R_3=R_4=H$; $A=-(CH_2)_9-$

The title compound was obtained in 100% yield by operating as in Example 1 but using 1,9-bis thiomethyl nonane ($n_D^{20}$:1.4960) instead of 1,2-bis thiomethyl ethane. The identity and structure of this compound were confirmed by analysis as indicated after the examples. This compound is a liquid.

EXAMPLE 4

1,4-bis thiobenzyl butane, diborane $R_1=R_2=$benzyl; $R_3=R_4=H$; $A=-(CH_2)_4-$ The title compound was obtained in 94% yield by the method described in Example 1 but using 1,4-bis thiobenzyl butane ($n_D^{20}=1.5920$) instead of 1,2-bis thiomethyl ethane. The identity and structure of this compound were confirmed by analysis as indicated after the examples. This compound is white solid melting at from 88° C. to 91° C. (Koffler).

EXAMPLE 5

1,6-bis thiobenzyl hexane, diborane $R_1=R_2=$benzyl; $R_3=R_4=H$; $A=-(CH_2)_6-$ The title compound was obtained in 98% yield by the method described in Example 1 but using 1,6-bis thiobenzyl hexane ($n_D^{20}$:1.580) instead of 1,2-bis thiomethyl ethane. The identity and structure of this compound were confirmed by analysis as indicated after the examples. This compound is in the liquid form.

EXAMPLE 6

1,1-bis thio t.butyl methane, borane $R_1=R_2=$t.butyl; $R_3=R_4=H$ (1BH$_3$); $A=-CH_2-$ The title compound was obtained in 88% yield by the method described in Example 1 but using 1,1-bis thio t.butyl methane ($n_D^{25}=1.485$) instead of 1,2-bis thiomethyl ethane. The identity and structure of this compound were confirmed by analysis as indicated after the examples. This compound is a liquid.

EXAMPLE 7

1,2-bis thio t.butyl ethane, diborane $R_1=R_2=$t.butyl; $R_3=R_4=H$; $A=-(CH_2)_2-$ The title compound was obtained in 65% yield by the method described in Example 1 but using 1,2-bis thio t.butyl ethane ($n_D^{21}=1.486$) instead of 1,2-bis thiomethyl ehtane. The identity and structure of this compound were confirmed by analysis as indicated after the examples. This compound is a white solid melting at from 50° C. to 52° C. (Koffler).

EXAMPLE 8

1,2-bis thio t.butyl propane, diborane $R_1=R_2=$t.butyl; $R_3=R_4=H$; $A=$

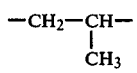

The title compound was obtained in 100% yield by the method described in Example 1 but using 1,2-bis thio t.butyl propane ($n_D^{23}=1.484$) instead of 1,2-bis thiomethyl ethane. The identity and structure of this compound were confirmed by analysis as indicated after the examples. This compound is a liquid.

EXAMPLE 9

1,2-bis thio t.butyl ethane, dithexylborane $R_1=R_2=$t.butyl; $R_3=H$; $R_4=$thexyl; $A=-(CH_2)_2-$ The title compound was obtained by adding to 0.05 mol of thexylborane (the purity of which had been verified by hydrolysis of an aliquot thereof) 5.15 g (0.025 mol) of 1,2-bis thio t.butyl ethane dissolved in 30 ml of methylene dichloride recently distilled on calcium hydride, maintaining the temperature at 25° C. The mixture was stirred for 4 hours at 25° C. and the solvent evaporated off under reduced pressure. The identity and structure of this compound were confirmed by analysis as indicated after the examples. Yield about 7 g. (70%). This compound is a liquid.

This compound is obtained under the following dimer form:

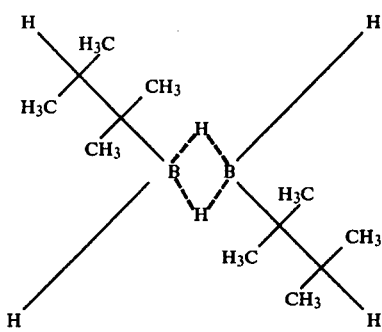

EXAMPLE 10

1,9-bis thio t.butyl nonane, dithexylborane $R_1=R_2=$t.butyl; $R_3=H$; $R_4=$thexyl; $A=-(CH_2)_9-$ The title compound was obtained in 75% yield by the method described in Example 9 but using 1,9-bis thio t.butyl nonane ($n_D^{21}=1.4802$) instead of 1,2-bis thio t.butyl ethane. The identity and structure of this compound were confirmed by analysis as indicated after the examples. This compound is in dimer form, is a liquid.

EXAMPLE 11

1,4-bis thiobenzyl butane, didisiamyl borane $R_1=R_2=$benzyl; $R_3=R_4=$disiamyl; $A=-(CH_2)_4-$ The title compound was obtained by adding to 25 ml (0.05 mol) of a 2M solution of disiamylborane in tetrahydrofuran (the purity of which had been verified by hydrolysis of an aliquot thereof) 7.6 g (0.025 mol) of 1,4-bis thiobenzyl butane, at room temperature. Stirring was maintained for 1 hour at 25° C., then 1 hour at 35° C. and then the solvent was evaporated off under reduced pressure. The identity and structure of this compound were confirmed by analysis as indicated after the examples. Yield 100% (15.3 g). This is a liquid product.

This compound is obtained under the following dimer form:

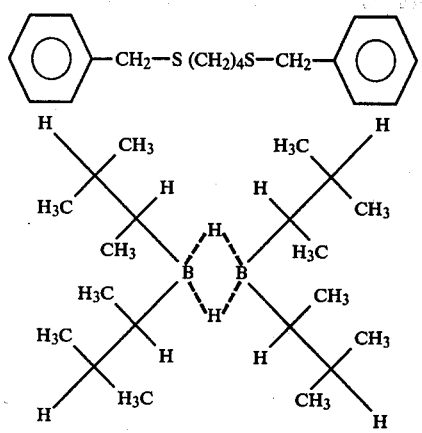

The stoichiometry and the purity of the complexes obtained in the examples are checked by methanolysis according to the technique described by J. BERES, A. DODDS, A. J. MORABITO and R. M. ADAMS, Inorg. Chem., 10, (9), 2072, (1971), and by microanalysis. The structure is confirmed by infra-red analysis showing absorption bands at from 2,400 cm$^{-1}$ to 2,350 cm$^{-1}$ (in CCl$_4$ at 2%) characteristic of B-H bonds of diborane complexes or at from 2,450 cm$^{-1}$ to 2,500 cm$^{-1}$ (weak) and 1,560 cm$^{-1}$ (strong) characteristic of B-----H-----B bonds of substituted diborane complexes (BROWN H. C., NEGISHI E., KATZ J. J. J. Am. Chem. Soc., 97, 2791, (1075). The structure is also confirmed by nuclear magnetic reasonance (H$^1$).

The stability of the complexes obtained according to this invention has been studied for many months and checked regularly by methanolysis, by infra-red spectrometry and also by comparison under reduced pressure of the gazeous decomposition; the comparison is made with boron dimethyl sulphide for compounds where the borane moiety is not substituted and with the corresponding substituted boranes for the compounds where the borane moiety is substituted. The products stored under nitrogen and at low temperature have not shown any alteration.

The activity and the interest of the compounds according to this invention have been checked in hydroboration reactions by the method described by L. M. BRAUN, R. A. BRAUN, H. R. CUISSMANN, M. OPPERMAN and R. M. ADAMS, J. Org. Chem., 36, (16), 2388, (1971) on cis 4-methyl 2-pentene, comparatively with the corresponding presently commercial available borane complexes; the excellent selectivity of action and the quantitative yield of hydroboration have been confirmed with, in all cases, higher speeds of reaction. The amounts of isomer alcohols obtained were determined by gas chromatography; the alcohols are synthesized by oxydation of the obtained organoborane with H$_2$O$_2$ or triethylamine N-oxide.

The activity of the compounds according to this invention has also been checked in reduction reactions, also by comparison with the corresponding commercially available borane complexes, using the methods of BROWN H. C. and SUBBA ROA B. C., J. Amer. Chem. Soc. 22, 1135, (1957) or BROWN H. C., BIGLEY D. B., ARORA S. K. and YOON N. H. J. Amer. Chem. Soc., 92, 7161, (1970) for instance with 2-methyl cyclohexanone as reference compound. In all cases, the results are as good as with the previously used corresponding reducing agents and confirm those found in the literature (CRAGG "Organoboranes in Organic Synthesis" Marcel Dekker Inc., New York, 1973, page 327), with the advantages of easier handling and better stability.

We claim:
1. A compound of the formula:

R$_4$R$_3$HB:R$_1$SASR$_2$:BHR$_3$R$_4$ wherein:
A stands for a straight, branched or cyclic hydrocarbon chain containing from up to 9 carbon atoms,
R$_1$ and R$_2$ stand each for a straight or branched alkyl rest containing up to 5 carbon atoms in the longest chain, or benzyl radicals optionally substituted by one or more lower alkyl containing up to 5 carbon atoms or a halogen, and
R$_3$ and R$_4$ stand for a hydrogen atom, a lower alkyl up to C$_6$ or a mono or bicycloalkyl group.

* * * * *

UNITED STATES PATENT AND TRADEMARK OFFICE
CERTIFICATE OF CORRECTION

PATENT NO. : 4,208,354
DATED : June 17, 1980
INVENTOR(S) : Claude Demosthene

It is certified that error appears in the above-identified patent and that said Letters Patent are hereby corrected as shown below:

Column 1, line 54: before "slightly" insert -- a --.

Column 2, line 15: change "1932" to "1392"

Column 2, line 25: omit "and reduction processes"

Column 6, line 39: omit "from"

Signed and Sealed this

Tenth Day of February 1981

[SEAL]

Attest:

Attesting Officer

RENE D. TEGTMEYER

Acting Commissioner of Patents and Trademarks